United States Patent [19]

Desbois et al.

[11] Patent Number: 4,876,376

[45] Date of Patent: Oct. 24, 1989

[54] PROCESS FOR THE HALOGENATION, NITRATION AND FLUORINATION OF AROMATIC DERIVATIVES

[75] Inventors: Michael Desbois, Rillieux; Camille Disdier, Lyons, both of France

[73] Assignee: Rhone-Poulenc Specialistes Chimiques, Courbevoie, France

[21] Appl. No.: 134,539

[22] Filed: Dec. 15, 1987

Related U.S. Application Data

[63] Continuation of Ser. No. 874,831, Jun. 16, 1986, abandoned, which is a continuation of Ser. No. 623,464, Jun. 22, 1984, abandoned.

[30] Foreign Application Priority Data

Jun. 23, 1983 [FR] France ................................ 83 10371

[51] Int. Cl.$^4$ .................. C07C 148/00; C07C 118/00; C07C 76/02
[52] U.S. Cl. ................................... 558/412; 558/411; 558/415; 558/416; 558/423; 558/425; 558/282; 560/358; 562/434; 562/435; 562/437; 562/438; 564/162; 564/166; 568/38; 568/44; 568/56; 568/58; 568/584; 568/585; 568/586; 568/587; 568/588; 568/929; 568/933; 568/937; 568/938
[58] Field of Search ............... 558/411, 412, 415, 416, 558/423, 425, 282; 560/358; 562/434, 435, 437, 438; 564/162, 166; 568/38, 44, 56, 58, 584, 585, 586, 587, 588, 929, 933, 937, 938

[56] References Cited

U.S. PATENT DOCUMENTS

| | | | |
|---|---|---|---|
| 3,326,983 | 6/1967 | Vesely et al. | 260/937 |
| 3,966,832 | 6/1976 | Lademann et al. | 570/145 |
| 4,061,688 | 12/1977 | Maul et al. | 570/145 |

FOREIGN PATENT DOCUMENTS

955898 4/1964 United Kingdom .
1206389 9/1970 United Kingdom .

OTHER PUBLICATIONS

Clarke, "Modern Organic Chemistry," pp. 433-434, (1964).
Weygand/Hilgetag, "Preparative Organic Chemistry," p. 150, (1972).
Kirk-Othmer, "Encyclopedia of Chemical Technology," vol. 21, 2nd Ed., p. 679.
Houben-Weyl, "Methoden der Organischen Chemie," vol. V/3, pp. 678-681, (1962).
Roberts, Chem. Abstr., vol. 18, p. 378, (1924).

*Primary Examiner*—Michael L. Shippen
*Attorney, Agent, or Firm*—Finnegan, Henderson, Farabow, Garrett & Dunner

[57] ABSTRACT

A process for the halogenation (bromination or chlorination)/nitration/fluorination of aromatic derivatives substituted by at least one group containing a halogenoalkyl unit. The aromatic derivative is reacted with a halogen and a nitrating agent in liquid hydrofluoric acid. The products obtained are useful as intermediates for the synthesis of compounds having a plant-protecting or pharmaceutical activity.

21 Claims, No Drawings

PROCESS FOR THE HALOGENATION, NITRATION AND FLUORINATION OF AROMATIC DERIVATIVES

This application is a continuation of application Ser. No. 874,831, filed June 16, 1986, now abandoned, which is a continuation of application Ser. No. 623,464, filed June 22, 1984, now abandoned.

The present invention relates to a process for the halogenation, nitration and fluorination of aromatic derivatives substituted by at least one group containing a halogenoalkyl unit. It relates more particularly to a process for the halogenation and nitration of the aromatic nucleus and to a process for the fluorination of the said group by halogen/fluorine exchange.

The term "halogenation" is understood as meaning the attachment of at least one chlorine or bromine atom to the aromatic nucleus.

The term "group containing a halogenoalkyl unit" is understood as meaning a group of the following formula:

$$-A-CX_1X_2Y$$

in which:
A represents a covalent bond, oxygen or sulfur,
$X_1$ and $X_2$, which are identical or different, represent a halogen and
Y corresponds to hydrogen, a halogen or an optionally halogenated alkyl chain having 1 to 3 carbon atoms.

The halogens corresponding to $X_1$, $X_2$ and Y are identical or different, but at least one of them must be other than fluorine.

For greater clarity, the halogen/fluorine exchange of the group containing a halogenoalkyl unit will be designated below by the term "fluorination-exchange".

It has been known for a long time to subject aromatic derivatives substituted by at least one group containing a halogenoalkyl unit, in a first step, to fluorination-exchange in hydrofluoric acid. The aromatic derivative substituted by at least one group containing a fluoroalkyl unit is then chlorinated, in a second, independent step, by means of a chlorination catalyst such as, in particular, $FeCl_3$, $BF_3$ (German Pat. No. 825,397) or Pt-on-alumina (German Pat. No. 1,034,609). Finally, the chlorinated aromatic derivative substituted by a fluoroalkyl group is nitrated, in a third step, by means of a nitric acid/sulfuric acid mixture as described in European patent application No. 54,464.

The fact that this is a three-step process has numerous disadvantages and, in particular, causes a loss of yield.

It has been possible, as described in Houben Weyl (volume 3, page 679), to combine the first two steps, namely chlorination and fluorination-exchange, into a single step using a catalyst such as antimony pentachloride in anhydrous hydrofluoric acid, but the nitration must then be carried out in an independent step.

The process described above has the advantage of proceeding in two steps, but it requires the presence of two catalysts, namely $SbCl_5$ for the first two steps and $H_2SO_4$ for the nitration; as $SbCl_5$ cannot be recycled, this presents problems of pollution from the technical point of view and problems of viability from the economic point of view.

The present invention, which overcomes the disadvantages of the prior art, relates to a process for the halogenation/nitration/fluorination-exchange of aromatic compounds substituted by at least one group containing a halogenoalkyl unit, which comprises reacting the said aromatic compound successively or simultaneously with a halogen and a nitrating agent in liquid hydrofluoric acid. Preferably, the inventive process is carried out in the same reaction enclosure, without intermediate treatment. For example, if nitration follows halogenation, there is no need to distill the halogenated product from the solution. Moreover, the entire inventive process can be carried out in one pot. The hydrofluoric acid serves a dual purpose; it acts as a fluorinating agent for the substituent group on the nucleus and acts as a solvent during the halogenation and nitration of the aromatic nucleus.

It is possible, according to the invention, to react the nitrating agent first and then the halogen, or the halogen and then the nitrating agent, or both simultaneously. It is preferred, however, to react the halogen first and then the nitrating agent.

If the reaction is carried out with the nitrating agent and then the halogen, as the nitrated aromatic derivative obtained is much less reactive, the reaction conditions for carrying out the halogenation must be more harsh. Furthermore, during the nitration, water is formed which causes partial hydrolysis of the halogenoalkyl group during the halogenation.

It is also possible to carry out the nitration and the halogenation simultaneously in hydrofluoric acid, but, in this case, a mixture of isomers is certain to be obtained, which is rarely an advantage from the industrial point of view.

From a practical point of view, it is therefore preferable to carry out the halogenation first and then the nitration.

The aromatic compound used within the scope of the invention preferably corresponds to the following formula (I):

$$Ar-(ACX_1X_2Y)_n \qquad (I)$$

in which:
Ar represents a monocyclic or polycyclic aromatic radical,
A, $X_1$, $X_2$ and Y have the meanings mentioned above and
n is equal to 1 or 2 and preferably equal to 1.
Ar preferably has the formula:

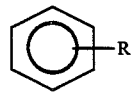

in which R represents a radical chosen from H, $NO_2$, CN, NCO, COOH, $CONH_2$, alkyl, alkoxy, phenyl and phenoxy.

The halogen and the nitro group will be attached to the nucleus according to the substitution rules well known to those skilled in the art, as a function of the presence of orthopara- or meta-directing radicals.

The fluorination-exchange makes it possible to exchange the halogens of halogenomethyl, halogenomethoxy and halogenothiomethyl groups to give $-CF_3$, $-OCF_3$ and $-SCF_3$.

In the case of halogenoalkoxy and halogenothioalkyl groups, the exchange will take place on the carbon located in the α-position to the heteroatom. Thus, the groups —OCCl$_2$—CCl$_3$ and —SCCl$_2$CCl$_3$ will be converted by fluorination-exchange to —OCF$_2$CCl$_3$ and —SCF$_2$CCl$_3$.

On the other hand, the halogen atoms directly attached to the benzene nucleus are not affected by the fluorination-exchange.

The hydrofluoric acid used for the present invention is preferably anhydrous hydrofluoric acid.

The molar ratio of the hydrofluoric acid to the starting aromatic compound is preferably between 10 and 100. An appreciably larger quantity does not have an adverse effect on the invention.

The quantity of halogen used is fixed by those skilled in the art, taking into account whether the desired product corresponds to monohalogenation or polyhalogenation. For monohalogenation, the reaction is preferably carried out in the presence of a stoichiometric deficit of halogen, that is to say with a molar ratio of halogen to aromatic compound preferably of between 0.5 and 0.9. For polyhalogenation, it is preferred to carry out the reaction with an excess of halogen. The halogen can be employed in a sealed enclosure under autogenous pressure (generally 1 to 50 bar) or under atmospheric pressure, for example by bubbling, or in any other device known to those skilled in the art.

The nitrating agent is chosen from nitric acid, alkali metal salts of nitric acid, and nitronium salts such as nitronium tetrafluoroborate, nitronium hexafluorophosphate and nitronium trifluoromethanesulfonate.

It is preferred to use concentrated or fuming nitric acid.

The nitric acid can also be generated in situ by reacting hydrofluoric acid with one of its salts.

In the case where the nitration is carried out before the halogenation, in order to minimize the hydrolysis phenomena, it is preferable to use a nitronium salt, nitronium tetrafluoroborate being preferred.

The molar ratio of the nitrating agent to the starting aromatic compound is preferably equal to at least 0.8 and even more preferably between 0.8 and 2.

If the nitration is carried out before the halogenation and if it is desired to effect mononitration, the molar ratio of nitronium salt to aromatic compound is preferably about 1.

The temperature at which the halogenation and the nitration are carried out is preferably between −20° and 150° C.

The reaction can take place at atmospheric pressure or under pressure.

If the temperature is to be above 20° C., the reaction will have to take place under pressure because the hydrofluoric acid must be liquid.

In the case where the halogenation is carried out first and the nitration afterwards, a practical way of carrying out the invention is to stop the halogen feed at the end of the halogenation reaction, to allow the unreacted halogen to escape, together, if appropriate, with the corresponding acid formed, and to introduce the nitric acid into the reaction medium without any other manipulation.

The duration of the chlorination and nitration reactions varies from a few minutes to a few hours.

The final product, which is a nitrated, halogenated aromatic derivative substituted by a fluoroalkyl group, can be extracted from the reaction medium by an organic solvent and then washed several times with water in order to remove all the hydrofluoric acid and all the remaining nitric acid.

In a preferred method of extraction, it is possible to distil all the hydrofluoric acid and then remove the nitric acid by washing the aromatic derivative with water.

Products of the formula (I) which may be mentioned are: trichloromethylbenzene, trichloromethoxybenzene, trichloromethylthiobenzene, chlorotrichloromethylbenzenes, fluorotrichloromethylbenzenes, dichlorobromomethylbenzene, tribromomethylbenzene, chlorotrichloromethoxybenzenes, fluorotrichloromethoxybenzenes, p-trichloromethylphenyl chloroformate, p-trichloromethylphenyl isocyanate, pentachloroethoxybenzene and pentachloroethylthiobenzene.

Although the invention is not limited to these compounds, it has a particularly advantageous application in the chlorination, nitration and fluorination-exchange of perchloroalkyl, perchloroalkoxy and perchlorothioalkyl aromatic derivatives such as, for example, trichloromethylbenzenes, trichloromethoxybenzenes and trichloromethylthiobenzenes.

A particularly advantageous product from the industrial point of view is trichloromethylbenzene because the chlorinated nitrated product can be used to prepare orthotrifluoromethylaniline, which is used as a synthesis intermediate in the preparation of compounds having a plant-protecting activity.

The nitrated, chlorinated aromatic derivatives substituted by a fluoroalkyl group are used as synthesis intermediates in the pharmaceutical, plant protection and dyestuffs industries.

The present invention will be understood more easily with the aid of the examples which follow, which are given by way of indication but without in any way implying a limitation.

EXAMPLE 1

100 ml (5 mol) of anhydrous hydrofluoric acid and 19.6 g (0.1 mol) of trichloromethylbenzene are introduced into a 250 ml reactor equipped with a magnetic stirrer bar and cooled to about 0° C. The reaction mixture is left to degas (evolution of hydrochloric acid) for one hour, with stirring, and the reactor is then closed and brought to a pressure of 5 bar at 20° C. with chlorine gas. The whole is then heated at 100° C. for 10 hours, with stirring.

After cooling to about 0° C. again, the reactor is decompressed and 6.9 g (0.11 mol) of 100% nitric acid are introduced dropwise. The reaction is left to proceed for 4 hours 30 minutes at 20° C. The crude reaction mixture then obtained is introduced onto 120 g of crushed ice. The heterogeneous mixture resulting from this treatment is extracted 3 times with 100 cm$^3$ of methylene chloride. After decantation, the organic phases are combined, washed with 2 times 100 cm$^3$ of softened water and dried. Analyses carried out by gas chromatography (% area), IR spectrometry and mass spectrometry give the following result:
m-nitrotrifluoromethylbenzene: 12.3% p0 2-nitro-5-chlorotrifluoromethylbenzene: 63.7%
other nitrochlorotrifluoromethylbenzenes: 24%.

EXAMPLE 2

The procedure is identical to that of Example 1, the compounds and conditions being as follows:
Anhydrous hydrofluoric acid: 50 g (2.5 mol)
p-Trichloromethylphenyl isocyanate: 23.6 g (0.1 mol)
Chlorine pressure: 4 bar at 20° C.

Chlorination temperature: 20° C.
Chlorination time: 6 hours
100% HNO₃: 7 g (0.11 mol eq)
Nitration temperature: 20° C.
Nitration time: 4 hours Analyses carried out by gas chromatography (% area), IR spectrometry and mass spectrometry give the following result:
carbamoyl fluorides of 4-trifluoromethyl-5-nitro-2-chloroaniline and 4-trifluoromethyl-6-nitro-2-chloroaniline: 73%

EXAMPLE 3

The procedure is identical to that of Example 1, the compounds and conditions being those given below and the treatment of the crude reaction mixture with ice being replaced with extraction of this crude mixture 2 times using 100 cm³ of carbon tetrachloride, these organic phases subsequently being treated in the normal way.
Anhydrous hydrofluoric acid: 100 g (5 mol)
Trichloromethoxybenzene: 21.2 g (0.1 mol)
Bromine: 16 g (0.1 mol)
Bromination temperature: 120° C.
Bromination time: 5 hours
66% HNO₃: 10.5 g (0.11 mol eq)
Nitration temperature: 50° C.
Nitration time: 4 hours Analyses carried out by gas chromatography (% area), IR spectrometry and mass spectrometry give the following result:
p-nitrotrifluoromethoxybenzene: 7%
2-nitro-4-bromotrifluoromethoxybenzene and 3-nitro-4-bromotrifluoromethoxybenzene: 48%

EXAMPLE 4

The procedure is identical to that of Example 1, the compounds and conditions being those given below and the treatment of the crude reaction mixture with ice being replaced with distillation of this crude mixture up to a bottom temperature of 80° C., under atmospheric pressure, in order to remove as much of the hydrofluoric acid solvent as possible.
Anhydrous hydrofluoric acid: 100 g (5 mol)
p-Chlorotrichloromethylbenzene: 23 g (0.1 mol)
Chlorine pressure: 4 bar at 20° C.
Chlorination temperature: 100° C.
Chlorination time: 4 hours
100% HNO₃: 6.3 g (0.1 mol)
Nitration temperature: 30° C.
Nitration time: 3 hours Analyses carried out by gas chromatography (% area), IR spectrometry and mass spectrometry give the following result:
3-nitro-4-chlorotrifluoromethylbenzene: 18%
2-nitro-4,5-dichlorotrifluoromethylbenzene and 3-nitro-4,5-dichlorotrifluoromethylbenzene: 56%

What is claimed is:

1. A process for the halogenation, nitration and fluorination of an aromatic compound corresponding to the formula:

Ar—(ACX₁X₂Y)ₙ 

in which:
Ar is a monocyclic or polycyclic aromatic radical which may contain at least one substituent other than said —(ACX₁X₂Y) group(s);
A is a covalent bond, oxygen or sulfur;
X₁ and X₂, which are identical or different, are a halogen;
Y is selected from the group consisting of hydrogen, a halogen and an optionally halogenated alkyl chain having 1 to 3 carbon atoms;
wherein the halogens corresponding to X₁, X₂ and Y are identical or different, but at least one of them is other than fluorine; and
n is equal to 1 or 2;
comprising the step of reacting, in the substantial absence of a halogenation or nitration catalyst other than liquid hydrofluoric acid, the aromatic compound simultaneously or successively with a halogen and a nitrating agent, in liquid hydrofluoric acid for a time sufficient to effect halogenation and nitration of the aromatic ring of said aromatic compound and to effect halogen-fluorine exchange on said —(ACX₁X₂Y) groups(s),
with the proviso that when A is oxygen or sulfur, the halogen-fluorine exchange occurs on the carbon atom located in the alpha-position to either the oxygen or sulfur atom.

2. The process of claim 1, wherein the halogenation occurs prior to the nitration.

3. The process of claim 3, wherein the halogen is chlorine or bromine.

4. The process of claim 1, wherein the halogen is chlorine or bromine.

5. The process of claim 1, wherein n is equal to 1.

6. The process of claim 7, wherein Ar corresponds to the formula:

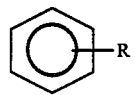

in which:
R is selected from the group consisting of H, NO₂, CN, NCO, COOH, CONH₂, alkyl, alkoxy, phenyl and phenoxy.

7. The process of claim 1, wherein Ar corresponds to the formula:

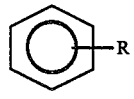

in which:
R is selected from the group consisting of H, NO₂, CN, NCO, COOH, CONH₂, alkyl, alkoxy, phenyl and phenoxy.

8. The process of claim 1, wherein the hydrofluoric acid is anhydrous.

9. The process of claim 1, wherein the molar ratio of hydrofluoric acid to aromatic compound ranges from 10 to 100.

10. The process of claim 9, wherein the molar ratio of hydrofluoric acid to aromatic compound ranges from 25 to 50.

11. The process of claim 1, wherein the nitrating agent is selected from the group consisting of nitric acid, alkali metal salts of nitric acid and nitronium salts.

12. The process of claim 11, wherein the molar ratio of nitrating agent to aromatic compound is at least 0.8.

13. The process of claim 1, wherein the molar ratio of nitrating agent to aromatic compound is at least 0.8.

14. The process of claim 12, wherein the molar ratio of nitrating agent to aromatic compound ranges from 0.8 to 2.

15. The process of claim 1, wherein the halogenation, the nitration and the halogen/fluorine exchange are carried out at from −20° C. to 150° C.

16. The process of claim 1, wherein the aromatic compound is selected from the group consisting of perchloroalkyl, perchloroalkoxy and perchlorothioalkyl derivatives.

17. The process of claim 16, wherein the aromatic compound is selected from the group consisting of trichloromethylbenzenes, trichloromethoxybenzenes and trichloromethylthiobenzenes.

18. The process of claim 1, wherein Ar corresponds to the formula:

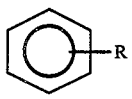

in which:
R is selected from the group consisting of hydrogen, halogen, $NO_2$, CN, NCO, COOH, $CONH_2$, alkyl, alkoxy, phenyl and phenoxy.

19. The process of claim 18, wherein R is a halogen selected from the group consisting of chlorine and fluorine.

20. The process of claim 1, wherein said reacting step is accomplished within one reaction enclosure without intermediate treatment.

21. The process of claim 1, wherein Ar is a monocyclic or polycyclic aromatic radical which may contain at least one substituent other than —$(ACX_1X_2Y)_n$, with the proviso that said substituent is selected from the group consisting of halogen, $NO_2$, CN, NCO, COOH, $CONH_2$, phenyl, phenoxy, and haloformate.

* * * * *